United States Patent
Choudhary et al.

(10) Patent No.: US 6,984,760 B2
(45) Date of Patent: Jan. 10, 2006

(54) ACYLATION OF AROMATIC COMPOUNDS

(75) Inventors: Vasant Ramchandra Choudhary, Pune (IN); Rani Jha, Pune, IN (US)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/814,849

(22) Filed: Mar. 31, 2004

(65) Prior Publication Data
US 2005/0222465 A1    Oct. 6, 2005

(51) Int. Cl.
*C07C 45/54*    (2006.01)

(52) U.S. Cl. .................. 568/321; 568/322; 568/323

(58) Field of Classification Search ............... 568/321, 568/322, 323
See application file for complete search history.

(56) References Cited

U.S. PATENT DOCUMENTS

| | | | |
|---|---|---|---|
| 6,437,191 B1 * | 8/2002 | Choudhary et al. | 568/319 |
| 6,459,000 B1 * | 10/2002 | Choudhary et al. | 568/319 |
| 6,525,226 B2 * | 2/2003 | Choudhary et al. | 568/323 |
| 6,548,722 B1 * | 4/2003 | Choudhary et al. | 585/467 |
| 2002/0120169 A1 | 8/2002 | Spagnol et al. | |
| 2003/0018219 A1 | 1/2003 | Choudhary et al. | |

FOREIGN PATENT DOCUMENTS

| | | |
|---|---|---|
| EP | 1 138 662 | 10/2001 |
| EP | 1 149 819 | 10/2001 |
| FR | 2 599 275 | 12/1987 |

* cited by examiner

*Primary Examiner*—Johann Richter
*Assistant Examiner*—Sikarl A. Witherspoon
(74) *Attorney, Agent, or Firm*—Ladas and Parry LLP

(57) ABSTRACT

This invention particularly relates to a process for the acylation of aromatic compounds by an acylating agent for preparing corresponding acylated aromatic compounds, using a solid catalyst.

14 Claims, No Drawings

ACYLATION OF AROMATIC COMPOUNDS

This invention relates to a process for the acylation of aromatic compounds with or without comprising a nitro group(s) using a solid catalyst. This invention particularly relates to a process for the acylation of aromatic compounds with or without comprising nitro groups by an acylating agent for preparing corresponding acylated aromatic compounds, using a reusable solid catalyst.

The process of this invention could be used for the preparation of acylated aromatic compounds with or without comprising nitro group(s), which are fine chemicals and/or used as intermediates in the preparation of fine chemicals or specialty chemicals in dyes and pharmaceutical industries and other chemical industries.

A number of homogeneous and heterogeneous solid catalyzed liquid phase processes based on Friedal-Crafts type reactions for the acylation of aromatic compounds without comprising nitro group(s) are known in the prior art.

Friedel-Crafts Type Acylation Reactions Catalyzed by Homogeneous Catalysts

The Friedal-Crafts type acylation of aromatic compounds without comprising nitro group(s) by various acylating agents, using homogeneous lewis acid catalysts, such as $AlCl_3$, $BF_3$, $ZnCl_2$ and other metal chlorides and protonic acid catalysts, such as $H_2SO_4$, $H_3PO_4$, HF, etc., are well known in the prior art.

In a U.S. patent [U.S. Pat. No. 5,476,970 (1995)], Rains et al. disclosed a homogeneous liquid phase process for the acylation of $R_1R_2C_6H_4$ by $R_3R_4C_6H_3COCl$, wherein $R_1$, $R_2$, $R_3$ and $R_4$ are non-nitro chemical groups, using $FeCl_3$ catalysts at high pressures. In French patents [FR 2768728 (1999) and FR 2768729 (1999)], Baudry et al. disclosed liquid phase homogeneous process for the benzoylation of anisole by benzoyl chloride using rare earth halides or uranyl halide.

In a Japanese patent [JP 08277241, A2 (1996)], Kunikata disclosed a liquid phase process for the acylation of phenol by phenyl acetyl chloride using a homogeneous $AlCl_3$ catalyst. Use of $AlCl_3$ as a homogeneous catalyst is also disclosed by Oono for the acylation of toluene with acetyl-chloride at high pressures in a Japanese patent [JP 09059205, A2 (1997)].

In a Japanese patent [JP 2000086570, A2 (2000)], Shoji et al. have disclosed a homogeneous liquid phase process for the acylation of toluene by acetyl fluoride using $HF-BF_3$ as a catalyst.

The main disadvantages of the Friedal-Crafts type acylation processes based on the use of above mentioned homogeneous acid catalysts are as follows:

1) The separation and recovery of the dissolved acid catalysts from the liquid reaction mixture is difficult.
2) The disposal of the used acid catalysts creates environmental pollution.
3) The homogeneous acid catalysts also pose several other problems such as high toxicity, corrosion, spent acid disposal and use of more than the stoichiometric amount.

Friedal-Crafts Type Acylation Reactions Catalyzed by Heterogeneous Solid Catalysts A few liquid phase processes for the acylation of aromatic compounds without comprising nitro group(s) by acyl halides using solid catalysts are known in the prior art.

In a Japanese patent [JP 01089894, A2 (1995)], Myata et al. disclosed a liquid phase process for the acylation of toluene with benzoyl chloride using ammonium chloride treated H-beta zeolite catalysts under reflux for 3 h to get para-acylated toluene with 28% yield.

In a French patent [FR 2745287, A1 (1997)], Barbier et al. disclosed liquid phase acylation of anisole by benzoyl chloride under reflux using neodymium chloride deposited on montmorillonite K-10 clay.

In the recent U.S. patents [U.S. Pat. No. 6,437,191 (2002) and U.S. Pat. No. 6,525,226 (2003)], Choudhary et al. disclosed process for the Friedel-Crafts type acylation of aromatic compounds without comprising nitro group(s), using reusable solid catalysts comprising indium chloride or reusable basic anionic clay catalysts.

Acylation of an aromatic compound involves electrophilic substitution of H from the aromatic nucleus of the aromatic compound. It is well known in the prior art that the electrophilic substitution is favored by the presence of electron donating groups, such as OH, alkyl, alkoxy, phenoxy, alkyl amine, SH, etc., in the aromatic compound. Whereas the electrophilic substitution is inhibited by the presence of electron withdrawing groups, such as halo, cyano, nitro, carboxy, aldehyde, etc., in the aromatic compound. Among the electron withdrawing groups, nitro group is the strongest electron withdrawing group and hence Friedel-crafts type alkylation or acylation of nitro compounds is very difficult and has not been reported so far in the prior art.

Although some limitations of the homogeneous acid catalyzed processes are overcome in the prior art heterogeneous solid catalyzed processes described above, the acylating activity of the solid acid catalysts used in the prior art processes is low, particularly for acylating aromatic compounds not containing electron donating groups, such as benzene, naphthalene, etc and/or for acylating nitro aromatic compounds. Most of the prior art homogeneous and heterogeneous acid catalysts are moisture sensitive, and hence demand moisture-free or thoroughly dried reactants, solvents and catalysts for the Friedal-Crafts type acylation processes. In presence of moisture in the reaction mixture, all the above homogeneous catalyst and most of the heterogeneous catalysts show poor activity in the Friedal-Crafts type acylation processes. Hence there is a great practical need for finding more efficient and also moisture insensitive and reusable solid catalyst for the acylation of aromatic compounds, including those containing strong electron withdrawing group, such as nitro group(s). This invention is, therefore, made with the following objects so that most of the drawbacks or limitations of the prior art homogeneous and heterogeneous catalyzed processes for the Friedal-Crafts type acylation reactions could be overcome:

1. Accordingly, the main object of this invention is to provide a liquid phase process for the acylation of aromatic compounds with or without comprising strongly aromatic ring deactivating nitro group(s), using a novel solid catalyst, which has high activity not only when the aromatic ring activating groups (i.e. electron donating groups such as alkyl, alkoxy, hydroxy, phenoxy, etc) are present in the aromatic ring to be acylated but also when the strong ring deactivating groups, such as nitro group, are present in the aromatic compounds to be acylated, so that the reaction temperature is low and/or time for completing the reaction is short.
2. Other important object of this invention is to provide a liquid phase process for the acylation of aromatic compounds with or without comprising nitro group(s), using a novel solid catalyst, which is easily separable and reusable in the process.

3. Another important object of this invention is to provide a solid catalyzed liquid phase process for the acylation of aromatic compounds with or without comprising nitro group(s) even in the presence of moisture in the reaction mixture.

Accordingly, this invention provides; a process for the acylation of an aromatic compound(I), with or without comprising nitro group(s), by an acylating agent(II), comprising at least one carbonyl group, using a reusable solid catalyst, which comprises, i) reacting under stirring a crystalline micro- or mesoporous inorganic solid comprising surface hydroxyl groups with at least one anhydrous metal halide selected from anhydrous halides of Al, Ga, In, Tl and Fe, dissolved in a non-aqueous solvent, with the metal halide to the inorganic solid weight ratio in the range from 0.01 to 1.0 in the presence or absence of a flowing inert gas at a temperature in the range from 20° C. to 200° C., such that the amount of metal halide(s) consumed in the reaction is at least 0.1 mmol per gram of the inorganic solid and also the amount of hydrogen halide evolved in this reaction is at least 0.1 mole per mole of the metal halide(s) consumed in the reaction;

ii) separating the resulting solid from the reaction mixture obtained from step(i), washing by the non-aqueous solvent and drying under moisture-free atmosphere;

iii) contacting in a stirred batch reactor a liquid reaction mixture comprising aromatic compound(I) and acylating agent(II) with the inorganic solid obtained from step(ii), designated as solid catalysts(III), at the following reaction conditions: the weight ratio of solid catalyst(III) to acylating agent(II) in the range from 0.005 to 1.0, the mole ratio of acylating agent(II) to aromatic compound(I) in the range from 0.01 to 10, the temperature in the range from 50° C. to 300° C. and the pressure at least atmospheric one;

iv) separating the solid catalyst(III) and isolating the product(s), and the reactants, aromatic compound(I) and acylating agent(II) from the reaction mixture; and v) recycling the solid catalysts(III) for its reuse to step(iii) in a subsequent reaction batch.

In the process of this invention, aromatic compound(I) is represented by formula:

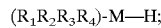

$(R_1R_2R_3R_4)$-M—H;

acylating agent(II) is represented by a formula:

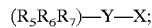

$(R_5R_6R_7)$—Y—X;

and the acylated compound produced is represented by a formula:

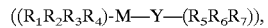

$((R_1R_2R_3R_4)$-M—Y—$(R_5R_6R_7))$, wherein, M is an aromatic nucleus such as single aromatic ring containing 6 C-atoms and 1 H-atom or fused two aromatic rings containing 10 C-atoms and 3H-atoms or three fused aromatic rings containing 14 C-atoms and 5H-atoms; $R_1, R_2, R_3$ and $R_4$ are chemical groups attached to the aromatic nucleus, M; Y, which is a nucleus of the acylating agent, is selected from C—CO, $C_nH_{2n-2}$CO, $C_6H_2$—CO, $C_6H_2C_nH_{2n}$—CO and $C_mH_{2m-4}$—CO; $R_5$, $R_6$ and $R_7$ are chemical groups attached to the nucleus of acylating agent, Y; X is a halogen or hydroxyl chemical group; H is hydrogen; C is carbon; O is oxygen; n and m are integer numbers having value above zero and above one, respectively. Each of the chemical groups, $R_1, R_2, R_3, R_4, R_5, R_6$ and $R_7$, may be selected from the following chemical groups: hydrogen, alkane, olefinic, phenyl, alkoxy, phenoxy, hydroxyl, aldehydic, ketonic, amine, amide, thio, sulphonic acid, nitro and cyano, groups and the like.

The process of this invention can be carried out in a stirred batch reactor, fitted with a reflux condenser and arrangement for bubbling inert gas through the reaction mixture, known in the prior art for carrying out liquid phase reactions.

In the process of this invention, the main product formed is corresponding acylated aromatic compound formed from the acylation by acylating agent(II) of aromatic compound(I) and a by-product HX, wherein, H=hydrogen and X=halogen or OH, depending upon the acylating agent used.

In the process of this invention, aromatic compound(I) and acylating agent(II) are reactants and are converted partially or completely to said products.

The process of this invention may be carried out with or without using a non-aqueous solvent, such as ethylene dichloride, nitromethane, n-hexane, n-heptane, n-octane or other solvents. In the process of this invention, the role of solvent, if used, is to dissolve solid reactant or reactants, to dilute reactants and/or to facilitate the reaction between aromatic compound and acylating agent. However, solvent may not be used in the process of this invention when both the reactants are liquids at said reaction conditions. Normally, said solvent is not converted in the process of this invention.

In the process of this invention, the role of inert gas bubbling continuously through the reaction mixture is to remove continuously said by-product from the reaction mixture so that the reverse reaction is avoided or minimized and the time required for completing the reaction is shortened. In the absence of bubbled inert gas, the reaction can still take place but with incomplete conversion and/or requiring longer period.

In the process of this invention, the role of the reflux condenser fitted with the reactor is to condense reactants and solvent, if used, and to return them back to the reaction mixture and allow the inert gas, which is continuously bubbling through the reaction mixture, along with said by-product to escape from the reaction mixture.

In the process of this invention, the reaction pressure above atmospheric pressure may be used to allow the reaction to be carried out at a temperature higher than the normal boiling point of the reactants and/or solvent, by increasing the boiling point of the said reactants and/or solvent with increasing the reaction pressure.

Solid catalyst(III), used in step (iii) of the process of this invention, is heterogeneous with respect to the reaction mixture and can be removed from the reaction mixture simply by filtration and the removed catalyst, after washing with solvent or said liquid aromatic compound, which is to be acylated, can be reused in step(iii) of the said process. The used catalyst of this process can be reused in step(iii) of the process several times. The reused catalyst shows high acylating activity in the process of this invention.

The role of the said solid catalyst(III) is to activate both the reactants—aromatic compound(I) and acylating agent (II) and thereby to increase rate of the acylation reaction in step(iii) of the process of this invention.

In the process of this invention, the preferred crystalline solid used in step(i) is Si-MCM-41 or crystalline cationic clay; the preferred cationic clay is montmorillonite; the preferred metal halide used in step(i) is anhydrous $AlCl_3$ and/or GaCl$_3$; the preferred non-aqueous solvent used in step(i) is carbon tetrachloride, dichloroethane or acetonitrile; the preferred inert gas used in step(i) is N$_2$, He or Ar; the preferred aromatic compound(I) used in step(iii) is nitrobenzene, dinitrobenzenes, nitro naphthalenes, substituted nitrobenzenes and substituted nitro naphthalenes; the preferred acylating agent(II) in step(iii) is benzoyl chloride, benzoyl bromide, acetyl chloride, acetyl bromide, substituted benzoyl chloride or substituted acetyl chloride; the preferred weight ratio of solid catalyst(III) to acylating agent(II) is between 0.05 and 0.5; the preferred mole ratio of acylating agent(II) to aromatic compound(I) is between 0.05 and 1.0; the preferred temperature employed in step (iii) is between 50° C. and 250° C.; the preferred pressure in step(iii) is between 1 atm and 10 atm.

By the process of this invention, nitrobenzene can also be benzoylated with benzoyl chloride to nitro benzophenone with 100% conversion of benzoyl chloride for a reaction period of less than 2 h.

The main finding of this invention is that, it is possible to directly acylate aromatic compounds, even those comprising highly aromatic ring deactivating nitro group(s), by an acylating agent, with a high conversion of the acylating agent, using a reusable solid catalyst by the process of this invention.

Other important finding of this invention is that, the solid catalyst of this invention can be easily separated from the reaction mixture, simply by filtration, and reused repeatedly in the process. Another important finding of this invention is that, the solid catalyst of this invention shows high activity in the Friedel-Crafts type acylation reactions of aromatic compounds with or without comprising nitro group(s), even in the presence of moisture.

The present invention is described with respect to the following examples illustrating the process of this invention for the acylation of aromatic compounds with or without comprising nitro group(s). These examples are provided for illustrative purposes only and are not be construed as limitation of the process of this invention.

Definition of Terms Used in the Examples

Conversion of reactants (%)=mole (%) of the reactant converted to all products. All the ratios of aromatic compounds(I) to acylating agent(II) are mole ratios. All the solid catalyst(III) to acylating agent(II) and solvent to aromatic compound(I) ratios are weight ratios.

The flow rates of gases are measured at 0° C. and 1 atm pressure. Gas hourly space velocity (GHSV) is volume of gas, measured at 0° C. and 1 atm pressure, passed through unit volume of the liquid reaction mixture per hour.

Ac and Aa represent aromatic compound(I) to be acylated and acylating agent(II), respectively.

EXAMPLE-1

This example illustrates the process of this invention for the acylation of nitrobenzene with benzoyl chloride, using a reusable solid catalyst of this invention.

The process of this invention, was carried out in the following five steps, as follows.

Step (i): 8.3 g of crystalline mesoporous high silica MCM-41, i.e. Si-MCM-4 having surface area of 1100 m$^2$g$^{-1}$, was taken in 100 cm$^3$ dry carbon tetrachloride. To this was added 6 mmol anhydrous AlCl$_3$ dissolved in 6 ml dry acetonitrile and 4 mmol anhydrous GaCl$_3$ dissolved in 4 ml dry carbon tetrachloride. The resulting reaction mixture was refluxed for 4 h under moisture-free N$_2$ (flow rate=60 ml/min). The gaseous hydrogen chloride evolved during the reaction between the Si-MCM-41 and chlorides of Al and Ga was measured quantitatively by absorbing it in aqueous NaOH solution by a simple acid-base titration using phenolphthalein indicator. The amount of HCl evolved in the reaction was 1.5 mmol.g$^{-1}$.

Step (ii): The reaction mixture was cooled and the solid catalyst is separated by filtration and washed by dry carbon tetrachloride, under moisture-free N$_2$ gas and dried under vacuum. The dried catalyst was analyzed for its Al and Ga content. The concentration of Al and Ga in the catalyst was 0.62 and 0.38 mmol.g$^{-1}$ respectively.

Step (iii): 0.4 g of the solid catalyst(III) obtained from step(ii), was contacted with a reaction mixture containing 13 ml (126 mmol) of nitrobenzene and 1 ml (8.6 mmol) benzoyl chloride in the absence of any solvent, in a stirred glass reactor (capacity: 25 cm$^3$) fitted with a reflux condenser, mercury thermometer dipped in the reaction mixture and an inlet tube for passing gas through the reaction mixture, under vigorous stirring, while bubbling moisture-fee N$_2$ gas at a flow rate of 30 ml.min$^{-1}$ through the reaction mixture at atmospheric pressure and at a temperature of 180° C. for 2 h. The gaseous hydrogen chloride evolved during the reaction was measured quantitatively by absorbing it in aqueous NaOH solution by a simple acid-base titration using phenolphthalein indicator. The amount of HCl evolved in the reaction was 8.5 mmol. The conversion of benzoyl chloride in the reaction was 99%.

Step (iv): The above reaction mixture was cooled to room temperature and the solid catalyst was seperated from the reaction mixture by filtration. The reaction product (benzoylated nitrobenzene) was isolated from the filtrate by column chromatography and characterized by spectroscopic techniques as nitro benzophenone.

Step (v): The solid catalyst obtained from step(iv) was washed with nitrobenzene and recycled in the step(iii) for reusing the catalyst for the benzoylation of nitrobenzene by benzoyl chloride at the reaction conditions same as that described earlier in the step(iii). The conversion of benzoyl chloride in this case was also found to be 99%, indicating reusability of the catalyst of the process of this invention. The Si-MCM-41 was prepared by the procedure given by Choudhary et al. (ref. Proceedings of Indian Academy of Sciences, (Chemical Sciences) volume 109, page 229 and year 1997).

EXAMPLES-2 to 7

These examples further illustrate the reusability of the catalyst of this invention, prepared in Example-1, several times in the process of this invention.

The reusability of the catalyst obtained from the step(v) of Example-1 was cared out by the same way as that described in Example-1 except that, the acylation reaction in step(iii) was carried out at different reaction conditions, as given in Table-1. In these examples, the aromatic compound to be acylated was nitrobenzene and the acylating agent was benzoyl chloride. The results are included in Table-1. These results show an excellent reusability of the catalyst of this invention in the process of this invention.

TABLE 1

Results showing the reusability of the catalyst prepared in Example-1 for the acylation of nitrobenzene by benzoyl chloride.

| Example Nos. | Example-2 | Example-3 | Example-4 |
|---|---|---|---|
| Catalyst (III) used | Catalyst after its use in Example-1 | Catalyst after its use in Example-2 | Catalyst after its use in Example-3 |
| Reaction conditions in step (iii) | | | |
| Solvent | nil | nil | nil |
| Ac/Aa mole ratio | 10.0 | 12.0 | 14.7 |
| Solvent/Aa mole ratio | 0 | 0 | 0 |
| Catalyst/Aa weight ratio | 0.3 | 0.4 | 0.3 |
| Temperature (° C.) | 180 | 180 | 180 |
| Pressure (atm) | 1 | 1 | 1.2 |
| GHSV of $N_2$ ($cm^3 min^{-1}$) | 30 | 30 | 30 |
| Reaction time (min) | 109 | 111 | 112 |
| Conversion of acylating agent (%) | 98 | 98 | 97 |
| Main product of reaction | $C_6H_5COC_6H_4NO_2$ | $C_6H_5COC_6H_4NO_2$ | $C_6H_5COC_6H_4NO_2$ |
| By product of reaction | HCl | HCl | HCl |

| Example Nos. | Example-5 | Example-6 | Example-7 |
|---|---|---|---|
| Catalyst (III) used | Catalyst after its use in Example-4 | Catalyst after its use in Example-5 | Catalyst after its use in Example-6 |
| Reaction conditions in step (iii) | | | |
| Solvent | nil | nil | nil |
| Ac/Aa mole ratio | 11.0 | 13.0 | 5.0 |
| Solvent/Aa mole ratio | 0 | 0 | 0 |
| Catalyst/Aa weight ratio | 0.3 | 0.3 | 0.2 |
| Temperature ° C. | 180 | 180 | 180 |
| Pressure (atm) | 1 | 1.1 | 1.6 |
| GHSV of $N_2$ ($cm^3 min^{-1}$) | 30 | 30 | 30 |
| Reaction time (min) | 115 | 120 | 124 |
| Conversion of acylating agent (%) | 97 | 97 | 96 |
| Main product of reaction | $C_6H_5COC_6H_4NO_2$ | $C_6H_5COC_6H_4NO_2$ | $C_6H_5COC_6H_4NO_2$ |
| By product of reaction | HCl | HCl | HCl |

EXAMPLES-8 to 25

These examples further illustrate the process of this invention for the acylation by different acyl halide of aromatic compounds with or without comprising nitro group(s).

The acylation was carried out by the procedure same as that described in Example-1 except that, the reactants and the reaction conditions employed in the step(iii) were different, as given in Table-2 and, in Examples 10, 12, 15 and 16, the solid catalyst obtained from step(ii) was stored over water in a desiccator at room temperature for 12 h before using it for the acylation reaction in step(iii). The results are included in Table-2.

The results show that aromatic compounds with or without comprising nitro group can be acylated by the process of this invention, even in the presence of moisture in the reactants, solvent and/or catalyst.

TABLE 2

Results of the acylation of aromatic compounds with or without comprising nitro group(s).

| Example Nos. | Example-8 | Example-9 | Example-10 |
|---|---|---|---|
| Reactants | | | |
| Aromatic compound (Ac) | Benzene | Naphthalene | Toluene |
| Acylating agent (Aa) | Benzoyl chloride | Benzoyl chloride | Benzoyl bromide |
| Reaction conditions in step (iii) | | | |
| Solvent | nil | n-Octane (saturated with water) | nil |
| Ac/Aa mole ratio | 15.0 | 5.5 | 14.2 |
| Solvent/Aa mole ratio | 0 | 1.0 | 0 |
| Catalyst/Aa weight ratio | 0.3 | 0.3 | 0.3 |
| Temperature ° C. | 80 | 120 | 110 |
| Pressure (atm) | 1 | 1 | 1 |

TABLE 2-continued

| | | | |
|---|---|---|---|
| GHSV of $N_2$ (cm$^3$min$^{-1}$) | 30 | 30 | 30 |
| Reaction time (min) | 99.0 | 88.5 | 65.0 |
| Conversion of acylating agent (%) | 68.5 | 73.2 | 9.0 |
| Main product of reaction | $C_6H_5COC_6H_5$ | $C_6H_5COC_{10}H_7$ | $C_6H_5COC_6H_4CH_3$ |
| By product of reaction | HCl | HCl | HBr |

| Example Nos. | Example-11 | Example-12 | Example-13 |
|---|---|---|---|
| Reactants | | | |
| Aromatic compound (Ac) | Anisole | Cumene (saturated with water) | Mesitylene |
| Acylating agent (Aa) | Benzoyl chloride | Benzoyl chloride | Benzoyl chloride |
| Reaction conditions in step (iii) | | | |
| Solvent | nil | nil | nil |
| Ac/Aa mole ratio | 13.9 | 10.9 | 10.0 |
| Solvent/Aa mole ratio | 0 | 0 | 0 |
| Catalyst/Aa weight ratio | 0.3 | 0.3 | 0.3 |
| Temperature °C | 140 | 140 | 145 |
| Pressure (atm) | 1 | 1 | 1 |
| GHSV of $N_2$ (cm$^3$min$^{-1}$) | 30 | 30 | 30 |
| Reaction time (min) | 9.0 | 4.1 | 7.0 |
| Conversion of acylating agent (%) | 99 | 100 | 100 |
| Main product of reaction | $C_6H_5COC_6H_4OCH_3$ | $C_6H_5COC_6H_4CH(CH_3)_2$ | $C_6H_5COC_6H_2(CH_3)_3$ |
| By product of reaction | HCl | HCl | HCl |

| Example Nos. | Example-14 | Example-15 | Example-16 |
|---|---|---|---|
| Reactants | | | |
| Aromatic compound (Ac) | p-Xylene | Nitrobenzene (saturated with water) | Nitrobenzene |
| Acylating agent (Aa) | Benzoyl chloride | Benzoyl chloride | Acetyl chloride |
| Reaction conditions in step (iii) | | | |
| Solvent | nil | nil | nil |
| Ac/Aa mole ratio | 12.3 | 14.7 | 9.0 |
| Solvent/Aa mole ratio | 0 | 0 | 0 |
| Catalyst/Aa weight ratio | 0.3 | 0.3 | 0.4 |
| Temperature °C | 140 | 180 | 40 |
| Pressure (atm) | 1 | 1 | 1 |
| GHSV of $N_2$ (cm$^3$min$^{-1}$) | 30 | 30 | 30 |
| Reaction time (min) | 10.0 | 105.0 | 6.9 |
| Conversion of acylating agent (%) | 99.9 | 99 | 100 |
| Main product of Reaction | $C_6H_5COC_6H_3(CH_3)_2$ | $C_6H_5COC_6H_4NO_2$ | $C_6H_5COC_6H_4COCH_3$ |
| By product of reaction | HCl | HCl | HCl |

| Example Nos. | Example-17 | Example-18 | Example-19 |
|---|---|---|---|
| Reactants | | | |
| Aromatic compound (Ac) | o-nitrotoluene | m-nitrotoluene (saturated with water) | p-nitrotoluene |
| Acylating agent (Aa) | Benzoyl chloride | Benzoyl chloride | Benzoyl chloride |
| Reaction conditions in step (iii) | | | |
| Solvent | nil | nil | Nil |
| Ac/Aa mole ratio | 5.0 | 4.9 | 4.2 |
| Solvent/Aa mole ratio | 0 | 0 | 0 |
| Catalyst/Aa weight ratio | 0.3 | 0.3 | 0.3 |
| Temperature °C | 140 | 150 | 150 |
| Pressure (atm) | 1 | 1 | 1 |
| GHSV of $N_2$ (cm$^3$min$^{-1}$) | 30 | 30 | 30 |
| Reaction time (min) | 155.0 | 189.2 | 137.0 |
| Conversion of acylating agent (%) | 86.8 | 100 | 58 |
| Main product of reaction | o-nitrotoluene phenyl ketone | o-nitrotoluene phenyl ketone | o-nitrotoluene phenyl ketone |
| By product of reaction | HCl | HCl | HCl |

TABLE 2-continued

| Example Nos. | Example-20 | Example-21 | Example-22 |
|---|---|---|---|
| Reactants | | | |
| Aromatic compound (Ac) | 1-chloro-3-nitro-benzene | 1-chloro-4-nitrobenzene | 1-bromo-3-nitro-benzene |
| Acylating agent (Aa) | Benzoyl chloride | Benzoyl chloride | Benzoyl chloride |
| Reaction conditions in step (iii) | | | |
| Solvent | nil | nil | Nil |
| Ac/Aa mole ratio | 3.7 | 3.7 | 3.0 |
| Solvent/Aa mole ratio | 0 | 0 | 0 |
| Catalyst/Aa weight ratio | 0.3 | 0.3 | 0.3 |
| Temperature °C. | 140 | 140 | 140 |
| Pressure (atm) | 1 | 1 | 1 |
| GHSV of $N_2$ ($cm^3 min^{-1}$) | 30 | 30 | 30 |
| Reaction time (min) | 149 | 94.5 | 219 |
| Conversion of acylating agent (%) | 69.4 | 63.6 | 75 |
| Main product of reaction | 1-Chloro-3-nitro-benzene phenyl ketone | 1-Chloro-4-nitrobenzene phenyl ketone | 1-bromo-4-nitro-benzene phenyl ketone |
| By product of reaction | HCl | HCl | HCl |

| Example Nos. | Example-23 | Example-24 | Example-25 |
|---|---|---|---|
| Reactants | | | |
| Aromatic compound (Ac) | Nitrobenzene (saturated with water) | 4-nitro acetophenone | 4-nitro benzaldehyde |
| Acylating agent (Aa) | Phenylacetyl chloride | Benzoyl chloride | Benzoyl chloride |
| Reaction conditions in step (iii) | | | |
| Solvent | Nil | nil | Nil |
| Ac/Aa mole ratio | 16.6 | 3.5 | 4.0 |
| Solvent/Aa mole ratio | 0 | 0 | 0 |
| Catalyst/Aa weight ratio | 0.3 | 0.3 | 0.3 |
| Temperature °C. | 90 | 130 | 130 |
| Pressure (atm) | 1 | 1 | 1 |
| GHSV of $N_2$ ($cm^3 min^{-1}$) | 30 | 30 | 30 |
| Reaction time (min) | 5 | 29.8 | 75 |
| Conversion of acylating agent (%) | 100 | 100 | 99 |
| Main product of reaction | Nitrobenzene Benzyl ketone | 4-nitroacetophenone phenyl ketone | 4-benzaldehyde phenyl ketone |
| By product of reaction | HCl | HCl | HCl |

EXAMPLES-26 to 28

These examples also illustrate the process of this invention for the acylation of different aromatic compounds with or without comprising nitro group(s).

The process was carried out similar to that described in Examples-8 to 25 except that, in the step(i), 10 Mmol of anhydrous $GaCl_3$ was used instead of 6 mmol of anhydrous $AlCl_3$ and 4 mmol of anhydrous $GaCl_3$. The reactants and reaction conditions used in step(iii) are given in Table-3. The results are included in Table-3. In this case, the amount of HCl evolved in step(i) was 1.2 $mmol.g^{-1}$ and the concentration of Ga and Cl in the dried catalyst obtained from the step(ii) was 0.65 and 0.61 $mmol.g^{-1}$ respectively.

TABLE 3

Results of the acylation of aromatic compounds with or without comprising nitro group(s).

| Example Nos. | Example-26 | Example-27 | Example-28 |
|---|---|---|---|
| Reactants | | | |
| Aromatic compound (Ac) | p-Xylene | Nitrobenzene | Toluene |
| Acylating agent (Aa) | Benzoyl chloride | Benzoyl chloride | Benzoyl chloride |
| Reaction conditions in step (iii) | | | |
| Solvent | nil | nil | Nil |
| Ac/Aa mole ratio | 12.3 | 14.7 | 14.2 |
| Solvent/Aa mole ratio | 0 | 0 | 0 |
| Catalyst/Aa weight ratio | 0.3 | 0.3 | 0.3 |
| Temperature ° C. | 140 | 180 | 110 |
| Pressure (atm) | 1 | 1 | 1 |
| GHSV of $N_2$ ($cm^3 min^{-1}$) | 30 | 30 | 30 |
| Reaction time (min) | 10.5 | 44.6 | 30.5 |
| Conversion of acylating agent (%) | 100 | 99 | 100 |
| Main product of reaction | $C_6H_5COC_6H_3(CH_3)_2$ | $C_6H_5COC_6H_4NO_2$ | $C_6H_5COC_6H_4CH_3$ |
| By product of reaction | HCl | HCl | HCl |

EXAMPLES-29 to 31

These examples also illustrate the process of this invention for the acylation of different aromatic compounds with or without comprising nitro group(s).

The process was carried out similar to that described in Examples-26 to 28 except, that in the step(i), 10 mmol of anhydrous $AlCl_3$ was used instead of 10 mmol of anhydrous $GaCl_3$. The reactants and reaction conditions used in step(iii) are given in Table-4. The results are included in Table-4. In this case, the amount of HCl evolved in step(i) was 2.3 $mmol.g^{-1}$ and the concentration of Al and Cl in the dried catalyst obtained from the step(ii) was 0.52 and 0.65 $mmol.g^{-1}$, respectively.

TABLE 4

Results of the acylation of aromatic compounds with or without comprising nitro group(s).

| Example Nos. | Example-29 | Example-30 | Example-31 |
|---|---|---|---|
| Reactants | | | |
| Aromatic compound (Ac) | p-Xylene | Nitrobenzene | Toluene |
| Acylating agent (Aa) | Benzoyl chloride | Benzoyl chloride | Benzoyl chloride |
| Reaction conditions in step (iii) | | | |
| Solvent | Nil | nil | nil |
| Ac/Aa mole ratio | 12.3 | 14.7 | 14.2 |
| Solvent/Aa mole ratio | 0 | 0 | 0 |
| Catalyst/Aa weight ratio | 0.3 | 0.3 | 0.3 |
| Temperature ° C. | 140 | 180 | 110 |
| Pressure (atm) | 1 | 1 | 1 |
| GHSV of $N_2$ ($cm^3 min^{-1}$) | 30 | 30 | 30 |
| Reaction time (min) | 24.5 | 14.2 | 10.5 |
| Conversion of acylating agent (%) | 100 | 100 | 95 |
| Main product of reaction | $C_6H_5COC_6H_3(CH_3)_2$ | $C_6H_5COC_6H_4NO_2$ | $C_6H_5COC_6H_4CH_3$ |
| By product of reaction | HCl | HCl | HCl |

EXAMPLES-32 to 34

These examples also illustrate the process of this invention for the acylation of different aromatic compounds with or without comprising nitro group(s).

The process was carried out similar to that described in Examples-8 to 25 except that, in the step(i), Montmorillonite K-10 was used instead of the Si-MCM-41. The reactants and reaction conditions used in step(iii) are given in Table-5. The results are included in Table-5.

TABLE 5

Results of the acylation of aromatic compounds with or without comprising nitro group(s).

| Example Nos. | Example-32 | Example-33 | Example-34 |
|---|---|---|---|
| Reactants | | | |
| Aromatic compound (Ac) | p-Xylene | Nitrobenzene | Toluene |
| Acylating agent (Aa) | Benzoyl chloride | Benzoyl chloride | Benzoyl chloride |
| Reaction conditions in step (iii) | | | |
| Solvent | Nil | nil | nil |
| Ac/Aa mole ratio | 12.3 | 14.7 | 14.2 |
| Solvent/Aa mole ratio | 0 | 0 | 0 |
| Catalyst/Aa weight ratio | 0.3 | 0.3 | 0.3 |
| Temperature ° C. | 140 | 180 | 110 |
| Pressure (atm) | 1 | 1 | 1 |
| GHSV of $N_2$ ($cm^3 min^{-1}$) | 30 | 30 | 30 |
| Reaction time (min) | 5.5 | 18.2 | 35.5 |
| Conversion of acylating agent (%) | 100 | 100 | 98 |
| Main product of reaction | $C_6H_5COC_6H_3(CH_3)_2$ | $C_6H_5COC_6H_4NO_2$ | $C_6H_5COC_6H_4CH_3$ |
| By product of reacton | HCl | HCl | HCl |

The novel features and main advantages of the process of this invention over the prior art process for the acylation of aromatic compounds with or without comprising nitro group (s) are as follow:

1) By the process of this invention, it is possible to directly acylate aromatic compounds, even that containing highly aromatic ring deactivating nitro group (s), with a high conversion of the acylating agent, using reusable solid catalyst. In the prior art direct acylation of aromatic compound containing nitro group(s) has not been accomplished; it was believed to be very difficult.
2) Apart from the above, the process of this invention has number of other advantages over the earlier homogeneous acid catalyzed processes for the Friedel-Crafts type acylation of aromatic compounds with or without comprising nitro group(s), are as follows:
    i) The catalyst used is heterogeneous solid catalyst and hence can be separated easily from the reaction products simply by filtration.
    ii) The separated catalysts can be reused in the process for a number of times, and
    iii) Also the catalyst is non corrosive;

Hence, most of the serious problems associated with homogeneous catalyst used in the earlier homogeneous catalyzed processes for the preparation of acylated aromatic compounds are overcome in the process of this invention.

3) The process of this invention has also number of advantages over the prior art processes based on the use of solid acid catalyst for the acylation of aromatic compounds, as follows:

i) The activity of the said solid catalyst used in the process of present invention is very high and hence the reaction is very fast and thereby the time required for completing the reaction is very short.
    ii) The catalyst of this invention can be reused repeatedly in the process and the reused catalyst shows high activity in the process even after its repeated use for a number of times in the process.
    iii) The process of the present invention can be used for acylating both small and large size aromatic compounds with both small and large size acylating agents to produce the corresponding acylated compounds.
    iv) In the process of this invention, when inert gas is bubbled through the reaction mixture continuously, said by-product formed in the reaction is removed continuously, and thereby the reverse acylation reaction is avoided or minimized, thus requiring short time for completing the reaction.
    v) In the process of this invention, by using pressure higher than 1 atm, it is possible to carry out the acylation reaction at a temperature higher than the normal boiling point of either of the reactants and the solvent, and thereby the reaction period for completing the reaction is shortened and/or the inhibition of the reaction due to strong adsorption of the reactants, products or solvent on the catalyst is avoided or minimized.
    vi) By the process of this invention, even the acylation of nitrobenzene, which is considered to be not possible due to its strong electron withdrawing nature, is possible, at mild conditions, with high conversions and hence the reaction is accomplished at a short reaction period.
    vii) Also, by the process of this invention, even the acylation of benzene and/or naphthalene, which does not contain any aromatic ring electron-donating group such as allyl, alkoxy, hydroxy, etc. group(s), is rapid at mild reaction conditions and hence the reaction is accomplished at a short reaction period.
    viii) In the process of this invention, by using the said solid catalyst, a rapid acylation of aromatic compounds with or without comprising nitro group(s) is possible even when the reaction mixture contains moisture; the catalyst is not deactivated due to the presence of moisture in the catalyst or in the reaction mixture, instead there is a drastic improvement in the catalytic activity of the catalyst in the presence of moisture. Hence, unlike the prior art homogeneous and solid acid catalysts, the catalyst of this invention does not demand moisture-free conditions to be active in the process and hence there is no need to remove traces of moisture from the catalyst, reactants or solvent used in the process, and thereby the process of this invention becomes more economical.

We claim:

1. A process for the acylation of an aromatic compound $(R_1 R_2 R_3 R_4)$-M—H of formula (I), wherein M is a single aromatic ring of 6 carbon atoms, a fused aromatic ring containing 10 carbon atoms and comprising 2 aromatic rings or a fused aromatic ring of 14 carbons atoms and comprising three aromatic rings: $R_1, R_2, R_3$ and $R_4$ are chemical groups attached to the aromatic ring wherein $R_1, R_2, R_3$ and $R_4$ are selected from the group consisting of hydrogen, alkane, alkene, phenyl, alkoxy, phenoxy, hydroxyl, acyl, ketones, amine, amide, thio, sulphonic acid, nitro or cyano group; using an acylating agent of formula (II) $R_5 R_6 R_7$—Y—X wherein Y is a nucleus of an acylating agent and is selected from the group consisting of C—CO, $C_nH_{2n-2}CO$, $C_6H_2$—CO and $C_6H_2C_nH_{2n}$—CO, n is an integer greater than zero and m is an integer greater than zero, X is a halogen atom or a hydroxyl group, and $R_5 R_6$ and $R_7$ are chemical groups attached to the nucleus of the acylating agent and are selected from the group consisting of hydrogen, alkane, alkene, phenyl, alkoxy, phenoxy, hydroxyl, acyl, ketones, amine, amide, thio, sulphonic acid, nitro or cyano group wherein the acylating agent of formula (II) comprises at least one carbonyl group; and a reusable solid catalyst, which comprises the steps of, i) reacting under stirring a crystalline micro- or mesoporous inorganic solid comprising surface hydroxyl groups with at least one anhydrous metal halide selected from the group consisting of anhydrous halides of Al, Ga, In, Ti and Fe, dissolved in a non-aqueous solvent, with the metal halide to the inorganic solid weight ratio in the range from 0.01 to 1.0 in the presence or absence of a flowing inert gas at a temperature in the range from 20° C. to 200° C., such that the amount of metal halide(s) consumed in the reaction is at least 0.1 mmol per gram of the inorganic solid and also the amount of hydrogen halide evolved in the reaction is at least 0.1 mole per mole of the metal halide(s) consumed in the reaction;

ii) separating the resulting solid which is an organic solid catalyst from the reaction mixture obtained from step (i), washing with the non-aqueous solvent and drying under moisture-free atmosphere;

iii) contacting in a stirred batch reactor a liquid reaction mixture comprising aromatic compound (I) and acylating agent (II) with the inorganic solid catalyst obtained from step (ii) in catalytic amounts at the following reaction conditions: the weight ratio of solid catalyst to acylating agent (II) is in the range from 0.005 to 1.0, the mole ratio of acylating agent (II) to aromatic compound (I) is in the range from 0.01 to 10, the temperature is in the range from 50° C. to 300° C. and the pressure is at least one atmosphere;

iv) separating the solid catalyst and isolating the product(s), and the reactants, aromatic compound (I) and acylating agent (II) from the reaction mixture; and v) recycling the solid catalyst for its reuse in step (iii).

2. A process as claimed in claim 1 wherein, the crystalline solid used in step (i) is Si-MCM-41 or crystalline cationic clay.

3. A process as claimed in claim 2 wherein, the cationic clay is Montmorillonite.

4. A process as claimed in claim 1 wherein, the metal halide used in step (i) is anhydrous $AlCl_3$, $GaCl_3$ or a mixture thereof.

5. A process as claimed in claim 1 wherein, the non-aqueous solvent used in step (i) is carbon tetrachloride, dichloroethane or acetonitrile.

6. A process as claimed in claim 1 wherein, the reaction in step (i) is carried out in a flow of inert gas selected from $N_2$, He or Ar.

7. A process as claimed in claim 1 wherein, the amount of hydrogen halide evolved in the reaction in step (i) is between 0.5 to 3 mol per mole of the metal halide consumed in the reaction.

8. A process as claimed in claim 1 wherein, the amount of metal halide consumed in the reaction in step (i) is between 0.5 and 5.0 mmol per gram of the inorganic solid.

9. A process as claimed in claim 1 wherein, aromatic compound (I) used in step (iii) is selected from the group consisting of nitrobenzene, dinitrobenzenes, nitro naphthalenes, substituted nitrobenzenes and substituted nitro naphthalenes.

10. A process as claimed in claim 1 wherein, the acylating agent (II) used in step (iii) is selected from the group consisting of benzoyl chloride, benzoyl bromide, acetyl chloride, acetyl bromide, substituted benzoyl chloride or substituted acetyl chloride.

11. A process as claimed in claim 1 wherein, the weight ratio of solid catalyst to acylating agent (II) is between 0.05 and 0.5.

12. A process as claimed in claim 1 wherein, the mole ratio of acylating agent (II) to aromatic compound (I) is between 0.05 and 1.0.

13. A process as claimed in claim 1 wherein, the temperature in step (iii) is between 50° C. and 250° C.

14. A process as claimed in claim 1 wherein, the pressure in step (iii) is between 1 atm and 10 atm.

* * * * *